United States Patent [19]

Dengler

[11] Patent Number: 5,508,443
[45] Date of Patent: Apr. 16, 1996

[54] LIQUID PHTHALIC ANHYDRIDE RECOVERY PROCESS

[75] Inventor: Herbert P. Dengler, Baton Rouge, La.

[73] Assignee: Exxon Chemical Patents Inc., Wilmington, Del.

[21] Appl. No.: 241,876

[22] Filed: May 12, 1994

[51] Int. Cl.$^6$ ................................................ C07D 307/89
[52] U.S. Cl. ............................................. 549/248; 549/250
[58] Field of Search ..................................... 549/248, 250

[56] References Cited

U.S. PATENT DOCUMENTS

| | | | |
|---|---|---|---|
| 3,178,452 | 4/1965 | Smith et al. | 260/346.4 |
| 3,303,203 | 2/1967 | Melnstein | 260/346.7 |
| 3,380,896 | 4/1968 | Scheiber et al. | 203/77 |
| 3,397,121 | 8/1968 | Fitzgerald | 203/35 |
| 3,507,886 | 4/1970 | Suter et al. | 260/346.7 |
| 3,650,906 | 3/1972 | Gehrken et al. | 203/89 |
| 3,655,521 | 4/1972 | Gehrken et al. | 203/28 |
| 3,681,399 | 8/1972 | Barth | 260/346.4 |
| 3,725,211 | 3/1973 | Gehrken et al. | 203/74 |
| 4,285,871 | 8/1981 | Keunecke et al. | 549/250 |
| 4,568,427 | 2/1986 | Danz et al. | 203/42 |
| 5,214,157 | 5/1993 | Healy et al. | 549/250 |

FOREIGN PATENT DOCUMENTS 1121645  4/1956  France .......................................... 14/1

*Primary Examiner*—Bernard Dentz
*Attorney, Agent, or Firm*—Richard D. Jordan

[57] ABSTRACT

A process for separating phthalic anhydride from a vapor phase oxidation product by mixing and cooling the vapor phase oxidation product with recycled by-products which have freezing points lower than the freezing point of pure phthalic anhydride, thereby condensing and recovering a liquid phase phthalic anhydride product without the formation of an intermediate solid phase.

26 Claims, 7 Drawing Sheets

LIQUID PHTHALIC ANHYDRIDE RECOVERY PROCESS

The present invention generally relates to a method and system for continuously recovering liquid phase phthalic anhydride from a vapor phase oxidation product without the formation of a solid phase. In particular, phthalic anhydride is condensed and recovered from the vapor phase oxidation product by contacting this gaseous oxidation product with recycled maleic anhydride and/or other by-products so that the condensate has a lower freezing point than pure phthalic anhydride, thereby eliminating the need for switch condensers.

BACKGROUND OF THE INVENTION

Phthalic anhydride is an important commercial chemical useful in the manufacture of plasticizers, polyesters, alkyd resins and dyes.

Phthalic anhydride is typically produced from raw materials such as orthoxylene (o-xylene), petroleum naphthalene, and coal-tar naphthalene. The price of these raw materials and, as a direct result, the price of phthalic anhydride have fluctuated greatly depending upon supply and demand. Because the cost of the raw materials is a major factor in the price of phthalic anhydride, it is of great importance that any system used to produce phthalic anhydride capture as much of the resultant product as possible.

Phthalic anhydride can be successfully produced from any of a number of processes, i.e., (1) air oxidation of o-xylene in fixed-bed reactors, (2) air oxidation of petroleum or coal tar naphthalene in fixed-bed reactors, (3) fluid bed oxidation of o-xylene, (4) fluid bed oxidation of petroleum or coal tar naphthalene, and (5) liquid phase oxidation of o-xylene or naphthalene.

The general process scheme for the various vapor phase routes is to mix the hydrocarbon feed (in the vapor form) with compressed air and to feed the mixture to fixed-bed reactors which contain tubes packed with catalysts, e.g., vanadium oxide and titanium dioxide coated on an inert, nonporous carrier. When fluid bed reactors are used, the hydrocarbon feed in liquid form can be injected directly into the fluidized bed so that the air and the hydrocarbon are mixed in the reactor to produce a reactor effluent gas (i.e., the vapor phase oxidation product). The reactors are equipped with means for removing the heat of the oxidation reaction. The heat that is removed is used to generate steam.

After the vapor phase oxidation product exits either the fixed-bed or fluid bed reactors, it is cooled to cause the phthalic anhydride to condense. This allows separation of the phthalic anhydride from the gas stream. The phthalic anhydride is typically condensed as a solid. However, a two-stage condensation system can be used to first condense a portion of the phthalic anhydride as a liquid and then to condense the remainder as a solid.

Expensive switch condensers that operate alternatively on a cooling cycle and a heating cycle are used to collect the phthalic anhydride as a solid. The solid is then melted for removal from the condensers.

The use of switch condensers to separate crude phthalic anhydride from a vapor phase oxidation product is described in U.S. Pat. No. 5,214,157 (Healy et al.), issued May 25, 1993, which is incorporated herein by reference. The resultant vapor phase oxidation product is cooled close to the solidification point (131° C.) of phthalic anhydride and any condensed liquid is usually separated out before the remaining vapor enters the switch condensers. The switch condensers desublime the vapor phase oxidation product using the cold condenser oil, and then melt off the solid phase crude phthalic anhydride product using a hot condenser oil heated with steam. Both the hot condenser oil and cold condenser oil are pumped through switch condensers via horizontally disposed heat exchange tubes.

A substantial amount of impurities exit switch condensers as part of the vapor stream, whereas the crude phthalic anhydride product is plated out on the heat exchange tubes as a solid during the cooling step and exits the switch condensers at the bottom as a liquid during the melting step. This crude phthalic anhydride liquid is collected from the switch condensers in surge vessels before being pumped to storage for crude finishing to commercial product. The vapor gases from the switch condensers are sent to waste gas incinerators where the by-products are destroyed by oxidation to carbon dioxide and water. This can be done in combination with fuel gas to produce steam.

Unfortunately, switch condensers involve a significant portion of the capital and operating costs of a phthalic anhydride plant. The cost of each switch condenser, including installation, can exceed a million dollars. Also, switch condensers operate in a batch mode on 3–6 hours cycles to desublime solid phthalic anhydride on the heat exchange tubes.

The present inventor has developed a unique process scheme which avoids the need to use expensive switch condensers in order to recover the phthalic anhydride from the vapor phase oxidation product. This unique process continuously condenses and recovers phthalic anhydride in the liquid phase without the formation of an intermediate solid phase.

The continuous liquid recovery process of the present invention provides the following advantages over conventional switch condensers: (1) fewer pieces of processing equipment; (2) continuous versus batch mode of operation; (3) recovery of more than 99.7% of the phthalic anhydride from the vapor phase oxidation product versus 99–99.4% for switch condensers; (4) typical losses of 0.25 to 0.5% of the crude phthalic anhydride production in the light ends distillation following recovery by switch condensers are significantly reduced due to the recycle of the light ends cut; (5) since the process concentrates the by-products from a low vapor concentration (e.g., for the maleic anhydride from less than 0.1 mol % in the vapor to more than 50 mol % in the recovered liquid streams), the maleic and citraconic anhydrides and the benzoic acid by-products can be readily further concentrated and upgraded for commercial sales of these by-products; (6) the cost of maleic anhydride recover for sale is lower than for typical plants because the impurities such as citraconic anhydride can be rejected into the recycled impure maleic anhydride and eventually purged with the benzoic acid stream and (7) benefits the environment because the waste gas contains less by-products and less phthalic anhydride.

In addition, this process has advantages over solvent recovery processes in that only materials already present are used for the recycle. No new material is added. In addition to cost of a solvent, some of the solvent will escape to the environment. Also the solvent could adversely effect the product quality of the phthalic anhydride or recovered by-products. Even if the recovery step using an ester is added to this recovery process, only the alcohol portion of the molecule is extraneous to the process stream because the acid portion of the ester is made from one of the acids and/or anhydrides in the process stream.

SUMMARY OF THE INVENTION

A process for separating phthalic anhydride from a vapor phase oxidation product which comprises the steps of: (a) cooling the vapor phase oxidation product to a temperature of about 130° to 165° C.; (b) mixing and further cooling the vapor phase oxidation product of step (a) with at least one by-product stream having a freezing point which is lower than the freezing point of pure phthalic anhydride, thereby forming a liquid phase phthalic anhydride product having a freezing point lower than the freezing point of pure phthalic anhydride, and a first vapor stream; (c) separating the liquid phase phthalic anhydride product from the first vapor stream; (d) separating the liquid phase phthalic anhydride product into a crude phthalic anhydride stream and a first by-product stream; (e) cooling the first by-product stream to a temperature in the range between about 40° to 80° C.; (f) recycling at least a portion of the first by-product stream to step (b); (g) cooling the first vapor stream to a temperature in the range between about 40° to 80° C., thereby forming a second by-product stream and a second vapor stream; (h) separating the second by-product stream from the second vapor stream; and (i) recycling the second by-product stream to step (b).

Optionally, cooling step (g) and separating step (h) may all take place in a cooling tower which comprises countercurrent flowing vertically disposed tubes and a recirculating coolant, wherein the liquid phthalic anhydride crude product is taken out as bottoms and the remaining vapor phase is taken overhead.

This cooling tower may alternatively comprise multiple cooling zones.

The process for separating phthalic anhydride from a vapor phase oxidation product may also include a by-product (i.e. maleic anhydride) recovery step which includes the following steps: mixing vapor stream from a second flash step with an absorbent to form an absorbent containing by-product stream; separating the absorbent containing by-product stream into a desorbed by-product stream and a concentrated absorbent stream; and mixing the desorbed by-product stream with a by-product stream.

Optionally, the cooling, separation and maleic anhydride recovery steps can be combined within a cooling tower which comprises countercurrent flowing vertically disposed tubes, a recirculating coolant, and an ester absorbing section, wherein the liquid crude phthalic anhydride stream is taken out as bottoms, the ester containing stream is taken out as a side stream, and the vapor phase purge is taken overhead.

DESCRIPTION OF THE PREFERRED EMBODIMENTS

A continuous process for condensing and recovering phthalic anhydride (PAN) in a liquid phase from a vapor phase oxidation product of o-xylene, naphthalene or the like, and air is hereafter described.

The freezing point of pure phthalic anhydride is 268° F. (131° C.). Cooling the vapor phase oxidation product below this temperature in conventional switch condensers leads to the plating out of a solid phase phthalic anhydride on the heat exchange tubes within each switch condenser.

The formation of crude liquid phthalic anhydride product without the presence of an intermediate solid phase phthalic anhydride according to the present invention is accomplished by contacting the vapor phase oxidation product with recycled by-products (e.g., maleic anhydride (MAN)) which have a lower freezing point than pure phthalic anhydride, whereby the freezing point of the resultant liquid phase phthalic anhydride product (i.e., a product which comprises a mixture of phthalic anhydride, maleic anhydride and other by-products) is approximately 240° F. (115° C.) compared to a freezing point of 268° F. (131° C.) for pure phthalic anhydride itself. Therefore, so long as the temperature of the liquid phase phthalic anhydride product is maintained above this new freezing point, the phthalic anhydride will be recovered in the liquid phase even at temperatures which are below the freezing point of pure phthalic anhydride.

That is, the phthalic anhydride recovery process according to the present invention uses recycled maleic anhydride together with other by-products from its second flash unit and the maleic anhydride fractionation column to increase the concentration of by-products in the vapor phase oxidation product. As the vapor phase oxidation product is cooled, some of the maleic anhydride by-product condenses with the phthalic anhydride to form a liquid phase phthalic anhydride product. The condensed maleic anhydride lowers the freezing point of the liquid phase phthalic anhydride product below the freezing point of pure phthalic anhydride. By careful adjustment of the operating conditions, the formation of solid phthalic anhydride can be avoided.

Figure 6:
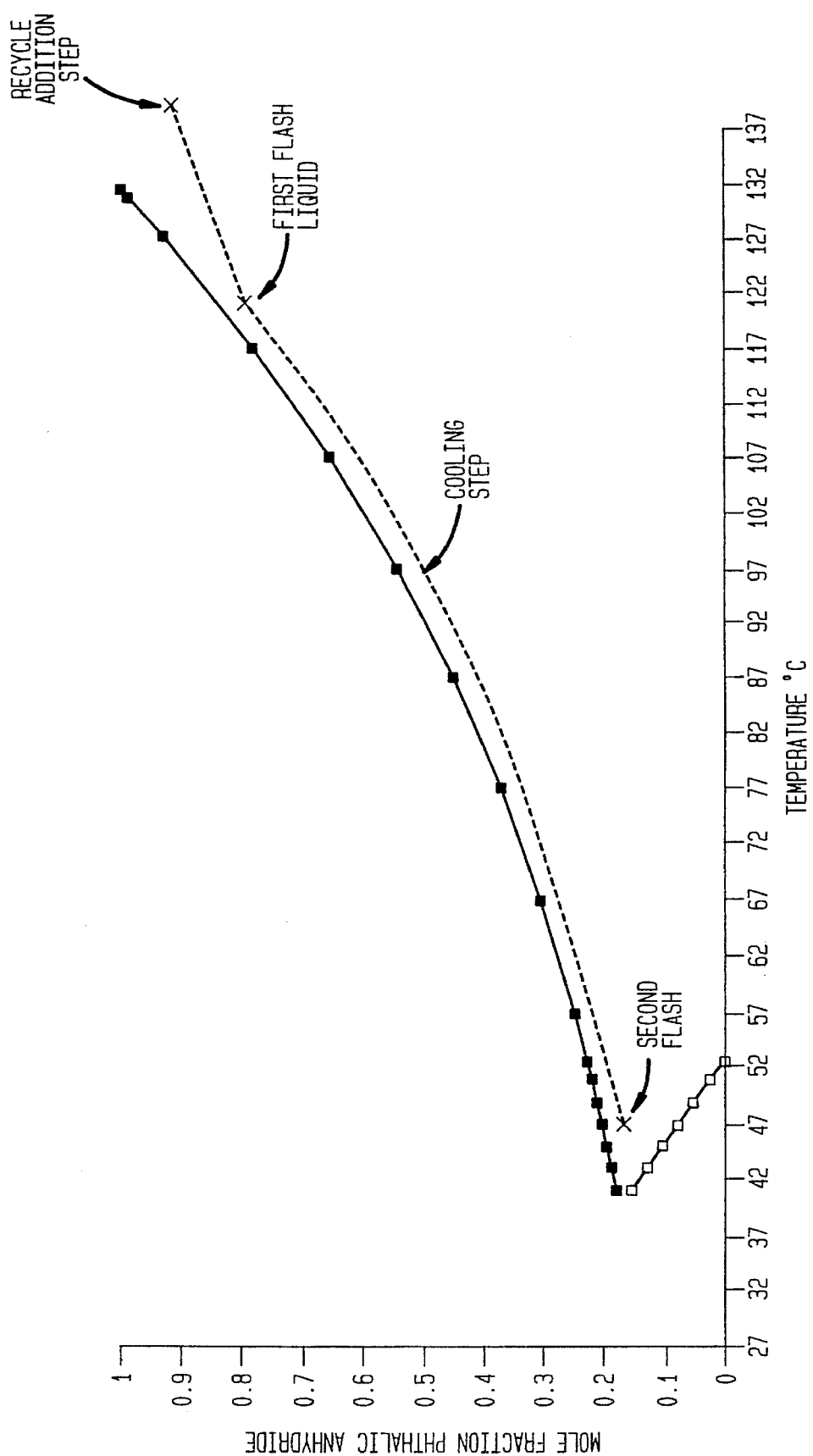
FIG. 6 is a graph plotting the mole fraction of phthalic anhydride contained within the crude liquid phthalic anhydride product versus the freezing point of the crude liquid phthalic anhydride product.

The freezing point of pure phthalic anhydride is 268° F. (131° C.) and that of the pure maleic anhydride is 127° F. (53° C.). As shown in FIG. 6, the minimum freezing point of a PAN/MAN mixture is about 104° F. (40° C.) at the eutectic composition of 17 mole % phthalic anhydride and 83 mole % maleic anhydride, based on estimates from heat capacity data. The presence of other materials such as citraconic anhydride in the vapor phase oxidation product further lowers the freezing point of the resultant liquid phase phthalic anhydride product.

Figure 1:
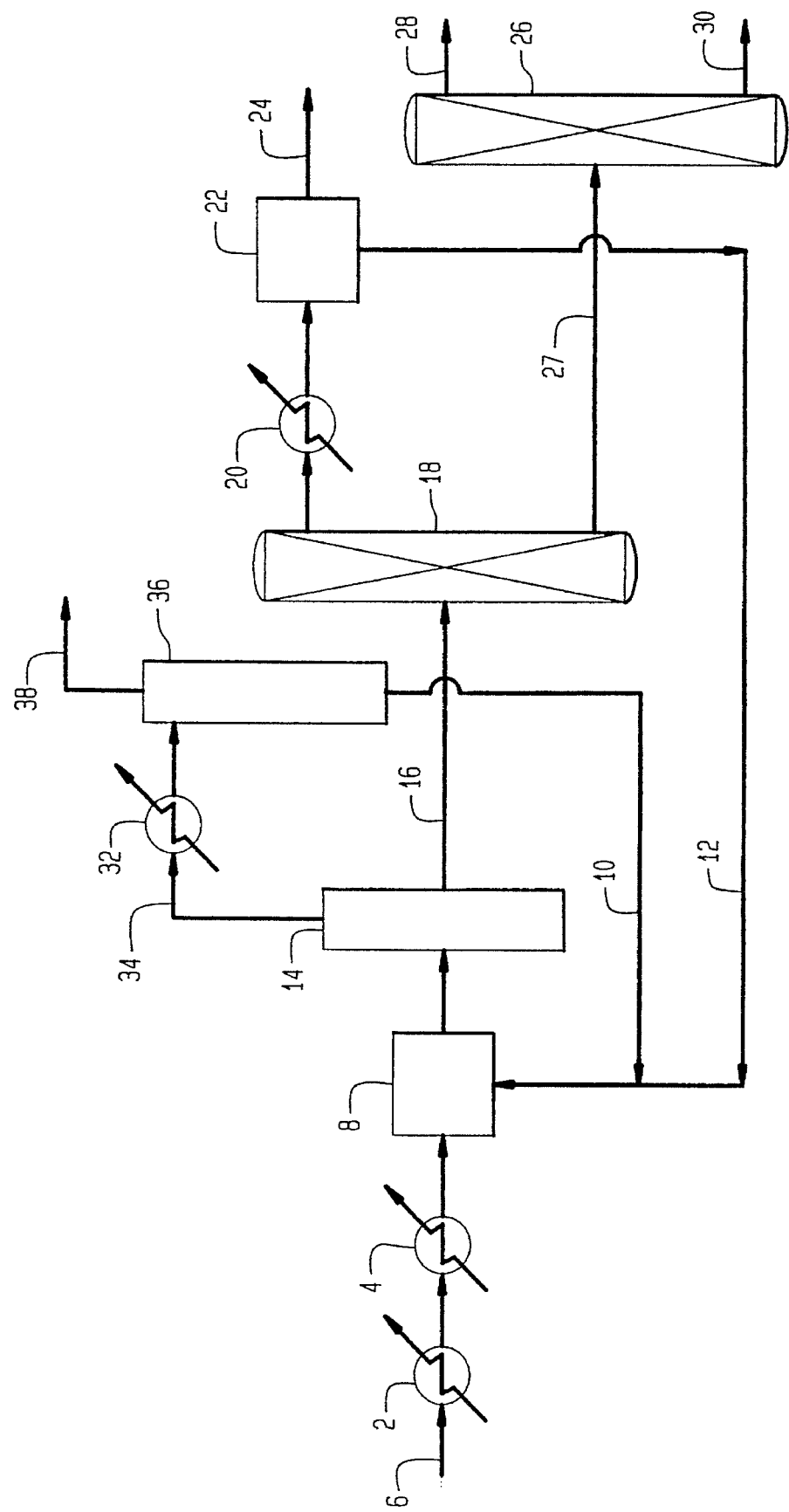
FIG. 1 is a schematic diagram of the phthalic anhydride recovery process in accordance with the present invention.

FIG. 1 is a schematic diagram of the liquid phthalic anhydride recovery process wherein the reactor effluent gas (e.g., a vapor phase oxidation product of o-xylene, naphthalene, and/or any other material capable of being catalytically converted to phthalic anhydride) is passed via conduit 6 through heat exchangers 2 and 4. After passing through heat exchanger 4 the vapor phase oxidation product has an approximate temperature of 280° F. (138° C.). The cooled vapor phase oxidation product is then sent to a mixing vessel 8 where it is combined with recycled by-products (e.g., maleic anhydride and citraconic anhydride) via conduits 10 and 12. This cools the vapor phase oxidation product to approximately 250° F. (121° C.) and condenses approximately 74–85% of the phthalic anhydride present within the gas. Normally, pure phthalic anhydride would have solidified at temperatures below 268° F. (131° C.), but the mixing of phthalic anhydride and at least one recycled by-product stream having a freezing point lower than pure phthalic anhydride (such as maleic anhydride) produces a liquid phase phthalic anhydride product having a lower freezing point than pure phthalic anhydride.

The liquid phase phthalic anhydride product is then separated from the remaining vapor phase which comprises maleic anhydride, residual phthalic anhydride and other volatile by-products via flash separation in flash unit 14.

The separated liquid phase phthalic anhydride product is then sent via conduit 16 to fractionation column 18 where maleic anhydride and other volatile by-products are separated. The overhead from fractionation column 18 is then passed through heat exchanger 20 and into stream splitter 22 wherein a portion of the liquid phase maleic anhydride and other by-products are recycled at approximately 140° F. (60° C.) via conduit 12 to mixing vessel 8. The remainder of the maleic by-product stream from splitter 22 is sent via conduit 24 for purge of benzoic acid and for downstream maleic recovery. Instead of a splitter, a distillation tower could be used to obtain a more concentrated purge stream and a higher purity maleic recycle by-product stream.

A phthalic anhydride enriched stream having less than 0.1% of benzoic acid is taken as bottoms from fractionation column 18 and sent to a second fractionation column 26 via conduit 27. In fractionation column 26, 99.8% pure phthalic anhydride product 28 is separated from higher boiling residue 30.

The vapor phase from flash unit 14 is sent to heat exchanger 32 via conduit 34 where it is cooled to approximately 116° F. (47° C.) before being sent to second flash unit 36. As the vapor is cooled and more liquid is condensed, the maleic anhydride concentration in the condensed liquid increases. The freezing point of the condensate continues to decline as the mixture cools so that no solidification occurs. At 116° F. (47° C.) the concentration of liquid is that of the eutectic which has a freezing point of about 105° F. (40° C.). The condensed liquid is separated from the remaining vapor in flash unit 36. This condensate is then recycled via conduit 10 to mixing vessel 8. The vapor phase is sent via conduit 38 to either maleic recovery or an incinerator (not shown). The vapor phase from flash unit 36 contains less than 0.3% of the phthalic anhydride originally present in the vapor phase oxidation product.

In cases where the entering maleic concentration is less than that in the vapor leaving the system, increasing the recycle of the other by-products, especially benzoic acid, increases the recovery of maleic anhydride to remain in material balance. Lowering the temperature in the flash units further increases the maleic anhydride recovery. Alternatively, the maleic anhydride leaving the system can be recovered for recycle.

Figure 2:
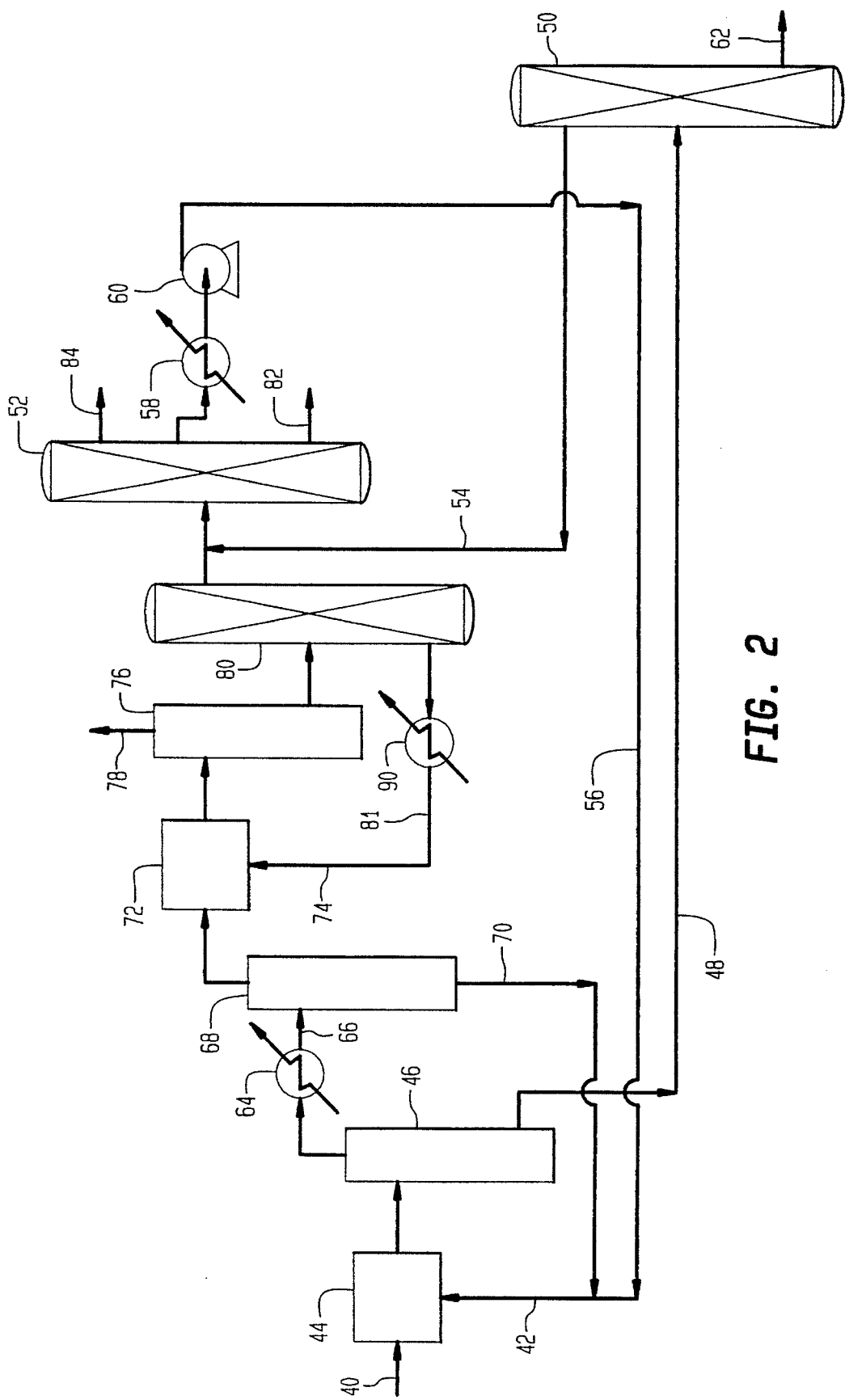
FIG. 2 is a schematic diagram of the phthalic anhydride recovery process in accordance with another embodiment of the present invention having a maleic anhydride recovery step.

FIG. 2 depicts a continuous liquid phthalic anhydride recovery process which includes a maleic anhydride recovery step. Vapor phase oxidation product having a temperature of approximately 282° F. (139° C.) and recycled by-products having a freezing point lower than that of pure phthalic anhydride are fed via conduits 40 and 42, respectively, into mixing vessel 44. The resulting mixture has a temperature of 250° F. (121° C.) and condenses approximately 70–90% of the phthalic anhydride present in the vapor phase oxidation product. The liquid condensate (i.e. the liquid phase phthalic anhydride product) is then separated from the vapor phase in flash unit 46.

The liquid phase phthalic anhydride product from flash unit 46 is then sent via conduit 48 to fractionation column 50 where benzoic acid and lighter components (i.e., more volatile components) are separated from a crude phase phthalic anhydride enriched stream which comprises phthalic anhydride and heavier components. The overhead from fractionation column 50 is then sent via conduit 54 for further distillation in fractionation column or tower 52. Fractionation column 52 purges benzoic acid and heavier components from the overall system before recycling the maleic-rich by-product stream to mixing vessel 44 via heat exchanger 58, pump 60 and conduit 56. The bottoms product from fractionation column 50 comprises a crude phthalic anhydride enriched stream. This crude phthalic anhydride enriched stream is discharged via conduit 62 and typically comprises less than 0.1% benzoic acid. Optionally, the discharge from conduit 62 can be sent to another fractionation column wherein 99.8% pure phthalic anhydride product can be separated from higher boiling residue.

The vapor phase effluent from flash unit 46 is further cooled to 118° F. (48° C.) via heat exchanger 64 to condense as much of the maleic anhydride as possible. The cooled product passes through conduit 66 into a second flash unit 68 wherein a condensation product of primarily maleic anhydride and smaller amounts of phthalic anhydride is recycled via conduit 70 to mixing vessel 44. The concentration of maleic anhydride has been adjusted by the operating conditions so that the condensed liquid is always above its freezing point.

In cases where the orthoxylene or naphthalene concentrations in air are low in the phthalic anhydride air oxidation reaction, the vapor-phase leaving the 118° F. (48° C.) flash unit 68 contains a higher amount of maleic anhydride than originally present in the vapor phase oxidation product. In these cases a maleic recovery step is added. The following describes a method for the recovery and recognizes that there are other methods which could be used. The vapor phase is passed from flash unit 68 to mixing vessel 72 where it is contacted with dihexylphthalate, or any other ester having a similar boiling point, supplied via conduit 74. The ester absorbs approximately 70% of the maleic anhydride which is present in the vapor phase. The maleic/ester mixture from vessel 72 is then passed to a flash unit 76. The residual vapor is separated and sent via conduit 78 to an incinerator (not shown). The liquid from flash unit 76 containing the absorbed maleic anhydride is separated from the ester via distillation in fractionation column or tower 80. This minimizes the amount of ester in the overhead maleic anhydride stream and especially in recycle stream 56. Virtually all of the ester remaining in the recovered maleic anhydride is removed via purge stream 82. Ester in recycle stream 56 would be purged as a heavy along with the phthalic anhydride residue, unchanged, but would increase the quantity of residue for disposal. The desorbed ester is passed through heat exchanger 90, and recycled to mixing vessel 72 via conduit 74.

Instead of esters, an alcohol such as hexyl alcohol or isopropyl alcohol could be used as make-up to the maleic recovery section. An alcohol which is capable of forming the monoester in-situ from maleic or phthalic anhydride and eventually forming the diester with similar adsorption properties to dihexyl phthalate would be a satisfactory substitute for the esters in the absorption of maleic anhydride.

The maleic anhydride recovered from the absorption step in fractionation column 80 is sent to fractionation column 52 along with overhead stream 54 from fractionation column 50. Fractionation column 52 has three product streams, i.e., bottoms, overhead and a recycle side stream. The bottoms are taken out via conduit 82 and primarily include benzoic acid and any heavier components rejected from fractionation column 50. Although not identified, trace components in this cut have been shown to cause color problems if not removed from the final purge stream. Essentially all of the ester make-up is rejected to this purge stream. The side stream 56 is an impure maleic anhydride recycle stream (i.e., a by-product stream) which contains no significant amounts of phthalic anhydride. Overhead 84 is a higher purity maleic anhydride stream suitable for upgrading for commercial sale.

overall recovery of the phthalic anhydride from the reactor effluent gas (i.e., vapor phase oxidation product) is approximately 99.7%. Unlike other recovery systems, essentially all of the benzoic acid in the reactor effluent gas is recovered and concentrated in purge stream 82. By increasing the amount of benzoic acid purged, the benzoic acid content in recycle stream 56 can be significantly reduced.

Figure 3:
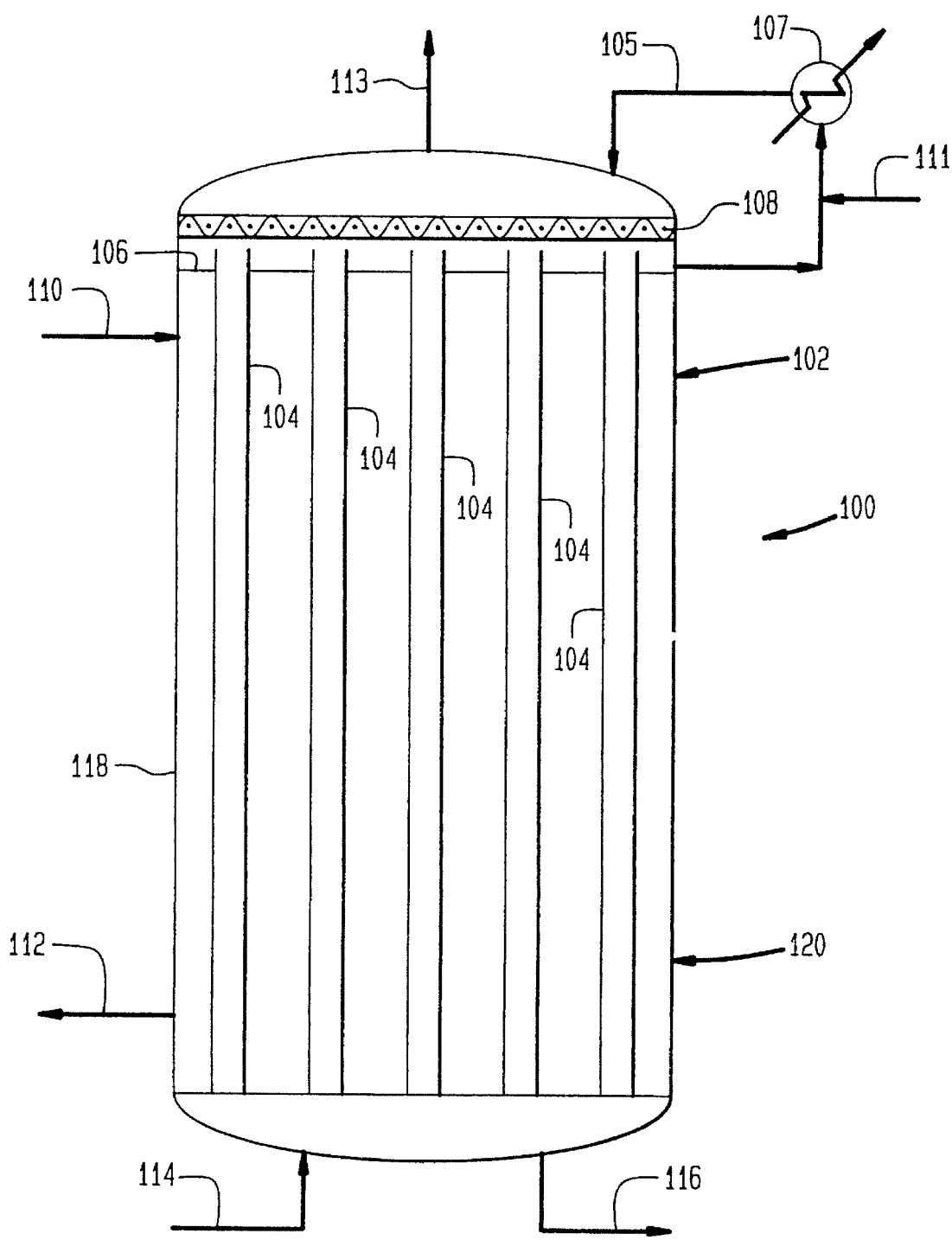
FIG. 3 is another embodiment in accordance with the present invention wherein a cooling tower is substituted for the cooling and second flash separation steps of the phthalic anhydride recovery process.

It is possible to combine cooling step 64 and flash steps 46 and 68 by using the countercurrent cooler tower shown in FIG. 3. Starting at the cold end 102 of cooler 100, tubes 104 extend beyond tubes sheet 106 similar to that of wetted wall column designs. A pumparound circuit 105 with a trim cooler 107 permits making vernier adjustments to the temperature. The recycled maleic anhydride stream is added to this circuit 105 via conduit 111. Part of the cooled pumparound is used to keep the de-entrainment screens 108 wet and provide good contacting with the vapor. Not only is entrainment reduced, but also an additional countercurrent contacting stage is obtained.

The main cooling is done by the coolant disposed within shell 118 of cooler 100. The coolant enters cooler 100 via conduit 110 and exits via conduit 112. The vapor phase from flash unit 46 enters cooler 100 via conduit 114 and the liquid phase phthalic anhydride product stream exits via conduit 116.

A close approach to the process stream in the cold end 102 is achieved by the use of heat transfer enhancers (not shown) in the tubes therein. The liquid on the top tube sheet 106 overflows into tubes 104 and is distributed evenly using typical wetted wall distributor designs. As the liquid moves down tube 104 it is heated by the rising vapor phase effluent supplied via conduit 114 and cooled by the coolant. As the stream gets hotter the maleic anhydride is recondensed with smaller amounts of phthalic anhydride setting up a large internal recycle of maleic anhydride. When the stream reaches 250° F. (121° C.), the concentrations will be that of the 250° F. (121° C.) flash unit. The remaining vapor phase exits cooler 100 via conduit 113 and is sent for further maleic recovery or incineration.

The coolant rate is controlled to produce a liquid phase phthalic anhydride product at 250° F. (121° C.)Heat transfer enhancers are not used in the bottom section 120 to minimize the possibility of freeze-ups by localized overcooling. In practice, the system tends to be self limiting. If too cold, solids will form on the tube surface which significantly decreases the localized cooling. Decreased cooling will reduce the amount of phthalic anhydride condensation which increases the concentration of maleic anhydride in the liquid phase which tends to wash away the solid deposits.

The concentration of the phthalic anhydride in the liquid phase at the cold end 102 of the exchanger (i.e., the pumparound composition) is monitored and maintained by addition of the recycled maleic stream via conduit 111. During start-up significantly higher amounts may have to be added until steady state is reached.

Figure 4:
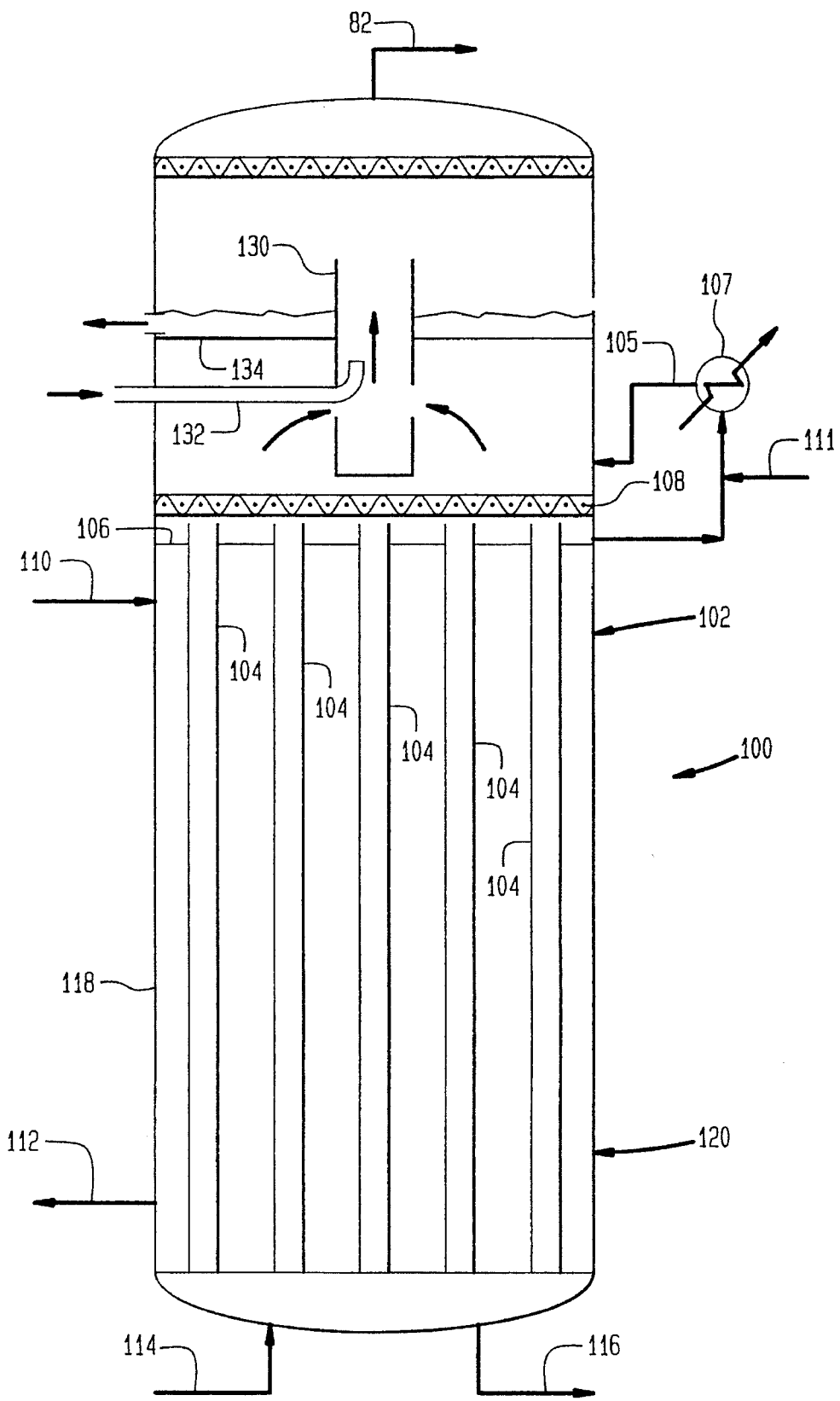
FIG. 4 is the cooling tower of FIG. 3 combined with an ester absorption step.

Since the organic content of the vapor phase oxidation product is typically less than 3 volume %, the volume of vapor phase is very large compared to the liquid organic stream condensed therefrom. Transporting such large volumes of gases requires the use of large diameter piping to minimize pressure drops throughout the process. As such, FIG. 4 depicts another embodiment according to the present invention wherein the ester absorption step is placed on top of the cooler shown in FIG. 3. This puts all of the large diameter equipment into one compact unit which minimizes pressure drop losses. In accordance with this embodiment, the vapor from tubes 104 pass through tubes sheet 106 into vapor channel 130 wherein it is contacted with an ester or ester convertible alcohol sprayed into the channel via distributor means 132. The resulting maleic/ester mixture collects along the bottom 134 of the ester recovery stage where it is sent on to fractionation column 80. The vapor phase is then sent via conduit 82 for disposal by incineration.

Figure 5:
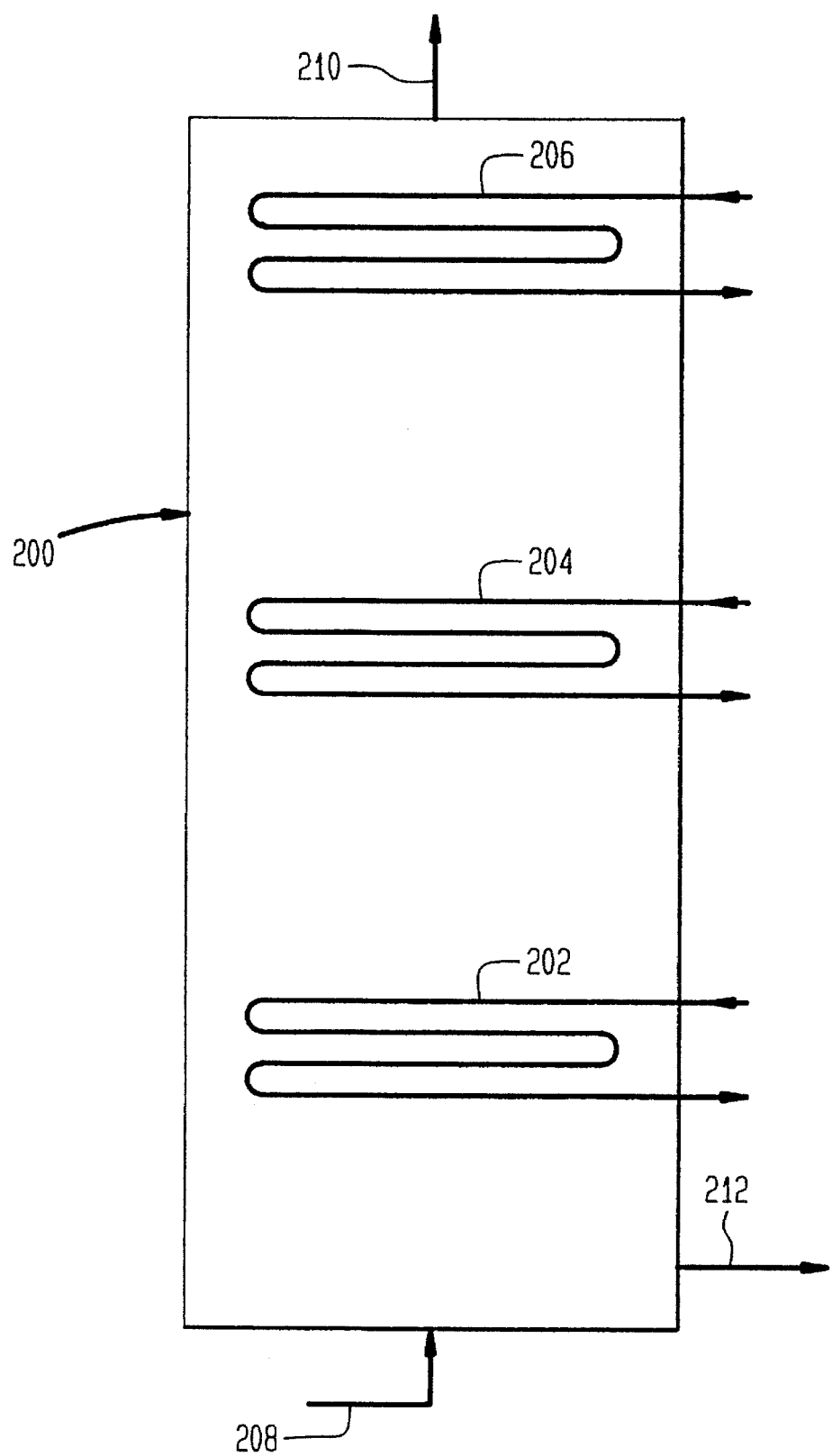
FIG. 5 is another embodiment in accordance with the present invention wherein a multi-zone cooling tower is substituted for the cooling and flash steps of the phthalic anhydride recovery process shown in FIG. 1.

FIG. 5 depicts another embodiment in accordance with the present invention wherein a packed or trayed cooling tower 200 is substituted for cooling means (32 or 64) and flash unit (36 or 68) and their connecting piping. Cooling tower 200 contains low pressure packing or trays to promote heat and mass transfer. Cooling tower 200 avoids the large pressure drops associated with multiple components and also provides the advantage of countercurrent operation which reduces the possibility of plugging and provides more efficient heat removal.

Cooling tower 200 includes cooling coils or trays 202, 204 and 206 which reduce the amount of recycle required. The cooled reaction effluent stream from cooler 4 is mixed with less recycle in mixer 8 or 44 and enters tower 200 via conduit 208 at a temperature of approximately 268° F. (131° C.). As the gas enters zone 1 of tower 200 it contacts cooling coil 202 which has a coolant passing therethrough having a temperature of approximately 210° F. (99° C.), thereby reducing the temperature of the gas to approximately 250° F. (121° C.). The gas then enters zone 2 where it contacts cooling coil 204 which has a coolant passing therethrough having a temperature of approximately 190° F. (88° C.), thereby further reducing the temperature of the gas to about 200° F. (93° C.). Finally, the gas enters zone 3 where it contacts cooling coil 206 having a coolant temperature of approximately 130° F. (54° C.). The final cooling step reduces the temperature of the gas to approximately 140° F. (60° C.). The remaining vapor phase is then sent via conduit 210 for maleic anhydride recovery or incineration. The liquid phase which is formed by the condensation product occurring within each zone of tower 200 is progressively enriched in phthalic anhydride as it moves down the tower. The liquid phase is removed from tower 200 via conduit 212 and recycled to the mixing stage (8 or 44).

Figure 7:
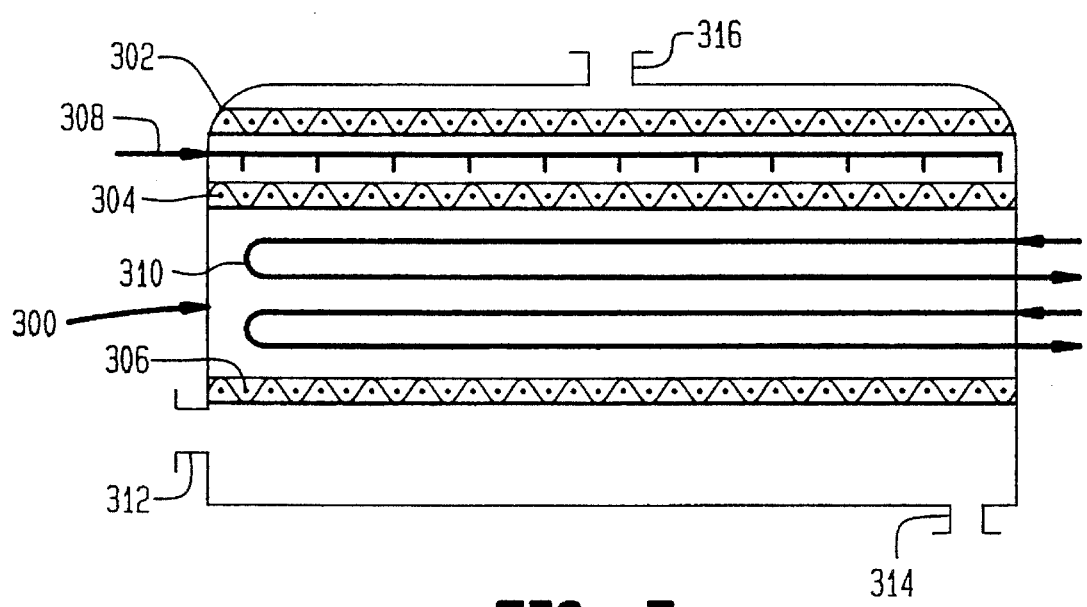
FIG. 7 is a schematic representation of a switch condenser which has been modified for use in recovering phthalic anhydride and maleic anhydride, respectively, in accordance with another embodiment of the present invention.

It would be cost effective if the conventional switch condensers were modified so that they could be adapted to recovering liquid phthalic anhydride and maleic anhydride with only small modification. Conventional switch condensers cool the effluent gases over about the same temperature range as needed for the liquid phthalic recovery process of the present invention. FIG. 7 shows a conventional switch condenser 300 which has been modified according to the present invention to include three layers of crinkled wire mesh screening 302, 304 and 306 (CWMS) or similar devices. The CWMS devices have been incorporated into switch condenser 300 in order to promote contacting and liquid distribution and to reduce entrainment.

In one embodiment the switch condenser 300 performs phthalic recovery, wherein maleic recycle (i.e., a eutectic mixture of maleic and phthalic anhydride) is sprayed over the top heat exchange tube bundle 310 using an existing spray wash distributor 308. As the cooled maleic mixture descends through each bundle 310 (typically 4 bundles) it contacts the hotter incoming gas which enters switch condenser 300 via inlet 312. The hotter incoming gas is also cooled by the oil flowing inside the heat exchange tube of bundles 310. As the liquid descends, it will increase in temperature and will become enriched in phthalic anhydride so its freezing point will increase. The phthalic enriched liquid is drained from switch condenser 300 via port 314 and has a temperature of approximately 250° F. (121° C.). This phthalic anhydride enriched liquid has the approximate composition of the first flash in the liquid phthalic recovery process at 250° F. (121° C.). The vapor phase from switch condenser 300 exits via port 316. This vapor phase has a temperature of approximately 120° F. (49° C.) and is sent to an incinerator or maleic recovery. Thus, the condenser accomplishes the phthalic anhydride recovery part of the liquid phthalic recovery process by combining the two flashes and intermediate cooling step in one vessel.

The oil rate in the liquid phthalic recovery process using switch condensers is controlled (i.e., limited) to obtain the desired temperatures and a countercurrent temperature profile (hotter at the bottom) which minimizes solids formation from freezing of the liquid. If some freezing were to occur this would self limit the cooling in that region due to the insulating effect of the solid. Deposits are of much less concern than in existing condensers because there is no temperature cycling and because the continuous liquid flow over the deposit would dissolve any acid formed as in the current spray washing.

In a second embodiment, switch condenser 300 can also be used for maleic anhydride recovery, wherein dihexylphthalate, or any other ester having a similar boiling point, is sprayed over the top of bundles 310 using the existing spray wash distributor 308. The vapor phase from the phthalic anhydride recovery process is introduced into switch condenser 300 via port 316. As the cooled maleic mixture descends through bundles 310 it contacts dihexylphthalate, or any other ester having a similar boiling point, and is also cooled by the oil flowing inside bundles 310. As the liquid descends the ester absorbs approximately 85% of the maleic anhydride which is present in the vapor phase. The ester/maleic mixture is thereafter forwarded via port 314 to a downstream desorption step and the residual gas is sent via port 312 to incineration.

Alternatively, the maleic anhydride absorption can be done countercurrently by introducing the gas in the bottom of the condenser and withdrawing it from port 316.

In still another embodiment, the desorption of the ester can be carried out in a condenser by using the hot oil circuit provided to melt out the desublimed phthalic anhydride. In this embodiment, the ester containing the maleic anhydride from the absorption step is sprayed over the switch condenser tubes as in the absorption step. Because the tubes are maintained at about 204.4° C. (400° F.) by the hot oil in the tubes, the maleic anhydride is desorbed and removed via port 312 or port 316. The desorbed ester after cooling is then returned to the maleic recovery step.

The process can then be conducted in three switch condensers using one for each of the three aforementioned embodiments. In the first, phthalic anhydride is recovered. The remaining vapor leaving the top of the condenser is connected via a short jump-over to a second adjacent condenser wherein the maleic anhydride is recovered from the vapor by absorption with ester. The maleic anhydride is then separated from the ester by heating in the third condenser. Thus, all three process steps can be accomplished using the existing equipment. This significantly reduces capital investment and downtime in conversion to the more efficient recovery process.

While I have shown and described several embodiments in accordance with my invention, it is to be clearly understood that the same are susceptible to numerous changes apparent to one skilled in the art. Therefore, I do not wish to be limited to the details shown and described but intend to show all changes and modifications which come within the scope of the appended claims.

What is claimed is:

1. A process for separating phthalic anhydride from a vapor phase oxidation product which comprises the steps of:

(a) cooling said vapor phase oxidation product to a temperature of about 130° C. to 165° C.;

(b) mixing and further cooling the vapor phase oxidation product of step (a) with at least one by-product stream having a freezing point which is lower than the freezing point of pure phthalic anhydride, thereby forming a liquid phase phthalic anhydride product having a freezing point lower than the freezing point of pure phthalic anhydride, and a first vapor stream;

(c) separating said liquid phase phthalic anhydride product from said first vapor stream by means of a flash separator;

(d) separating said liquid phase phthalic anhydride product into a crude phthalic anhydride stream and a first by-product stream;

(e) cooling said first by-product stream to a temperature in the range between about 40° C. to 80° C.;

(f) recycling at least a portion of said first by-product stream to said step (b);

(g) cooling said first vapor stream to a temperature in the range between about 40° C. to 80° C., thereby forming a second by-product stream and a second vapor stream;

(h) separating said second by-product stream from said second vapor stream by means of a flash separator; and (i) recycling at least a portion of said second by-product stream to said step (b).

2. The process according to claim 1 wherein said crude phthalic anhydride stream comprises less than 0.1% benzoic acid 3. The process according to claim 1 wherein said first by-product stream comprises at least one compound selected from the group consisting of: maleic anhydride, benzoic acid and citraconic anhydride.

4. The process according to claim 3 further comprising a step of separating said benzoic acid and said citraconic anhydride from said cooled first by-product stream of step (f) to form a maleic anhydride enriched stream and a purge stream comprising said benzoic acid and citraconic anhydride, wherein at least a portion of said maleic anhydride enriched stream is recycled to step (b).

5. The process according to claim 4 wherein the step of separating benzoic acid and citraconic anhydride from said first by-product stream takes place in at least one distillation column.

6. The process according to claim 1 wherein at least a portion of said first by-product stream is recycled to step (g).

7. The process according to claim 5 wherein a first distillation tower capable of producing a third by-product stream is followed by a second distillation tower capable of producing a fourth by-product stream.

8. The process according to claim 7 wherein at least a portion of said third by-product stream is returned to said step (b) and at least a portion of said fourth by-product stream is returned to said step (g).

9. The process according to claim 1 wherein steps (b) through (i) take place in a cooling tower which comprises countercurrent flowing vertically disposed tubes and a recirculating coolant, wherein said liquid phase phthalic anhydride product is taken out as bottoms and said second vapor stream is taken overhead.

10. The process according to claim 1 wherein steps (b), (e) and (g) through (i) take place in a cooling tower which comprises multiple cooling zones wherein said liquid phase phthalic anhydride product is taken out as bottoms and said second vapor stream is taken overhead.

11. A process for separating phthalic anhydride from a vapor phase oxidation product which comprises the steps of
  (a) cooling said vapor phase oxidation product to a temperature of about 130° C. to 165° C.;
  (b) mixing and further cooling the vapor phase oxidation product of step (a) with at least one by-product stream having a freezing point which is lower than the freezing point of pure phthalic anhydride, thereby forming a liquid phase phthalic anhydride product having a freezing point lower than the freezing point of pure phthalic anhydride and a first vapor stream;
  (c) separating said liquid phase phthalic anhydride product from said first vapor stream by means of a flash separator;
  (d) separating said liquid phase phthalic anhydride product into a crude phthalic anhydride stream and a first by-product stream;
  (e) cooling said first vapor stream to a temperature in the range between about 40° C. to 80° C., thereby forming a second by-product stream and a second vapor stream;
  (f) separating said second by-product stream and said second vapor stream by means of a flash separator;
  (g) recycling at least a portion of said second by-product stream to said step (b);
  (h) mixing said second vapor stream with an absorbent to form an absorbent containing by-product stream;
  (i) separating said absorbent containing by-product stream into a desorbed by-product stream and a concentrated absorbent stream;
  (j) mixing said desorbed by-product stream with said first by-product stream;
  (k) separating the mixture of step (j) into a fourth by-product stream and a purge stream comprising heavy by-products; and
  (l) recycling at least a portion of said fourth by-product stream to said step (b).

12. The process according to claim 11 further comprising a step of recycling at least a portion of said concentrated absorbent stream to step (h).

13. The process according to claim 11 wherein said absorbent is selected from the group consisting of: esters, and alcohols which are capable of forming monoesters and/or diesters in-situ.

14. The process according to claim 13 wherein said ester is dihexylphthalate.

15. The process according to claim 13 wherein said alcohol is hexyl alcohol.

16. The process according to claim 11 wherein said crude phthalic anhydride stream comprises less than 0.1% benzoic acid.

17. The process according to claim 11 wherein said crude phthalic anhydride stream comprises at least 99% of the phthalic anhydride present within said vapor phase oxidation product.

18. The process according to claim 11 wherein said purge stream of step (k) comprises benzoic acid, citraconic anhydride, and maleic anhydride.

19. The process according to claim 11 wherein said first, second, third and fourth by-product streams each include at least one compound selected from the group consisting of: maleic anhydride, benzoic acid and citraconic anhydride.

20. The process according to claim 11 wherein steps (b), (c) and (e) through (g) take place in a cooling tower which comprises countercurrent flowing vertically disposed tubes and a recirculating coolant, wherein said liquid phase phthalic anhydride product is taken out as bottoms and said second vapor stream is taken overhead.

21. The process according to claim 11 wherein steps (b), (c) and (e) through (i) take place in a cooling tower which comprises countercurrent flowing vertically disposed tubes, a recirculating coolant, and absorption section, wherein said liquid phase phthalic anhydride product is taken out as bottoms, said absorbent containing stream is taken out as a side stream, and said desorbed by-product stream is taken overhead.

22. The process according to claim 11 wherein steps (b), (c) and (e) take place in a cooling tower which comprises multiple cooling zones wherein said liquid phase phthalic anhydride product is taken out as bottoms and said second vapor stream is taken overhead.

23. A process fix separating phthalic anhydride from a vapor phase oxidation product which comprises mixing said vapor phase oxidation product having a temperature in the range of about 130° C. to 165° C. with a liquid maleic anhydride by-product under flash separation conditions wherein a liquid phase phthalic anhydride product containing between about 80 to 90 mole % phthalic anhydride and having a freezing point lower than the freezing point of pure phthalic anhydride, wherein at least a portion of the maleic anhydride contained with said mixture of said vapor phase oxidation product and said liquid maleic anhydride by-product is recovered as a vapor.

24. A process for separating phthalic anhydride from a vapor phase oxidation product M-rich comprises:
  (a) mixing said vapor phase oxidation product having a temperature in the range of about 130° C. to 165° C. with a liquid maleic anhydride by-product under flash separation conditions wherein a liquid phase phthalic anhydride product containing between about 80 to 90 mole % phthalic anhydride and having a freezing point lower than the freezing point of pure phthalic anhydride, wherein at least a portion of the maleic anhydride contained within said mixture of said vapor phase oxidation product and said liquid maleic anhydride by-product is recovered as a first vapor phase stream;

(b) separating at least a portion of said maleic anhydride by-product from said first vapor phase stream to form a maleic anhydride by-product stream and a second vapor phase stream;

(c) mixing said second vapor phase stream with an absorbent, thereby forming a maleic/absorbent stream; and (d) desorbing said maleic/absorbent stream to form an enriched maleic anhydride stream and a concentrated absorbent stream.

25. The process according to claim 1 wherein said liquid phase phthalic anhydride product which has been separated from said first vapor stream in step (c) has a phthalic anhydride concentration in the range between about 80 to 90 mole %.

26. The process according to claim 11 wherein said liquid phase phthalic anhydride product which has been separated from said first vapor stream in step (c) has a phthalic anhydride concentration in the range between about 80 to 90 mole %.

* * * * *